(12) United States Patent
Barrett et al.

(10) Patent No.: US 6,861,244 B2
(45) Date of Patent: Mar. 1, 2005

(54) INACTIVATED INFLUENZA VIRUS VACCINE FOR NASAL OR ORAL APPLICATION

(75) Inventors: Noel Barrett, Klosterneuburg/Weidling (AT); Otfried Kistner, Vienna (AT); Marijan Gerencer, Vienna (AT); Friedrich Dorner, Vienna (AT)

(73) Assignee: Baxter Healthcare S.A., Zurich (CH)

(*) Notice: Subject to any disclaimer, the term of this patent is extended or adjusted under 35 U.S.C. 154(b) by 7 days.

(21) Appl. No.: 10/639,449

(22) Filed: Aug. 13, 2003

(65) Prior Publication Data

US 2004/0096464 A1 May 20, 2004

Related U.S. Application Data

(63) Continuation of application No. 09/913,400, filed as application No. PCT/AT00/00023 on Feb. 1, 2000, now Pat. No. 6,635,246.

(30) Foreign Application Priority Data

Feb. 11, 1999 (AT) .............................................. 194/99

(51) Int. Cl.$^7$ ................................................ C12N 7/00
(52) U.S. Cl. .................................................. 435/235.1
(58) Field of Search ............................. 435/235.1, 237, 435/238, 239, 383, 395, 404; 424/209.1, 278.1

(56) References Cited

U.S. PATENT DOCUMENTS

| | | | |
|---|---|---|---|
| 4,981,782 A | 1/1991 | Judd et al. | 435/5 |
| 5,136,019 A | 8/1992 | Judd et al. | 530/326 |
| 5,243,030 A | 9/1993 | Judd et al. | 530/403 |
| 5,976,552 A | 11/1999 | Volvovitz | 424/199.1 |
| 6,635,246 B1 | 10/2003 | Barrett et al. | 424/93.6 |

FOREIGN PATENT DOCUMENTS

| | | |
|---|---|---|
| WO | WO97/49423 | 12/1931 |
| WO | WO94/19013 | 9/1994 |
| WO | WO96/15231 | 5/1996 |
| WO | WO96/40290 | 12/1996 |
| WO | WO99/24068 | 5/1999 |
| WO | WO00/15251 | 3/2000 |

OTHER PUBLICATIONS

Waldman, Nature 218: 594–595 (1968).
Wood, Journal of Biological Standardization 5: 237–247 (1977).
Avtushenko et al., Journal of Biotechnology 44: 21–28 (1996).
Belshe et al., New England Journal of Medicine 338(20): 1405–1412 (1998).
Chen et al., Current Topics in Microbiology and Immunology 146: 101–106 (1989).
Couch et al., Journal Infectious Diseases 176: 38–44 (1997).
Davenport et al., The Journal of Immunology 100(5): 1139–1140 (1968).
De Hann et al., Vaccine 13(2): 155–162 (1995).
Komase et al., Vaccine 16(2/3): 248–254 (1998).
Liew et al., Eur. J. Immunol. 14: 350–356 (1984).
Oka et al., Vaccine 8: 573–576 (1990).
Oka et al., Vaccine 12(14): 1255–1258 (1994).
Palmer et al., A Procedural Guide to the Performance of Rubella Hemagglutination–Inhibition Tests. U.S. Dept. of Health, Education, and Welfare, Immunology Series No. 2 Revised, pp. 25–62 (1977).
Tamura et al., The Journal of Immunology 149(3): 981–988 (1992).

Primary Examiner—Jeffrey Stucker
(74) Attorney, Agent, or Firm—Heller Ehrman White & McAuliffe LLP

(57) ABSTRACT

The invention relates to nasal or oral administration of a compound containing inactivated influenza virus antigen and aluminum as adjuvant for the prophylaxis of influenza virus infections. Said vaccine is especially suitable for inducing a mucosal IgA immune response and systemic IgG immune response.

6 Claims, No Drawings

INACTIVATED INFLUENZA VIRUS VACCINE FOR NASAL OR ORAL APPLICATION

This application is a continuation of U.S. Ser. No. 09/913,400 filed Dec. 5, 2001, now U.S. Pat. No. 6,635,246, which is 371 PCT/AT00/00023 filed Feb. 1, 2000, both of which are hereby incorporated by reference.

FIELD OF THE INVENTION

The invention relates to a vaccine composition containing at least one inactivated influenza virus antigen and aluminum as an adjuvant for nasal or oral application for the prophylaxis of influenza virus infections.

BACKGROUND OF THE INVENTION

Influenza virus infections represent an ever greater health risk, especially in the elderly and in persons with chronic diseases, because the infection in these groups often leads to higher mortality rates. Since the introduction in the 1940s of an inactivated influenza vaccine containing inactivated virus material from infected incubated eggs, the risk and course of the infection as well as the mortality rates in elderly persons have dropped.

To date, inactivated influenza virus vaccines from eggs are licensed for parenteral administration to people, and induce anti-HA-IgG antibodies in the serum. The cross-protection against heterologous influenza viruses, however, can be traced primarily to the cross-reactivity of IgA antibodies in a natural infection. (Liew et al., 1984, Eur. J. Immunol. 14:350–356). Therefore, with the development of new immunization methods against influenza virus infections, an attempt is being made to stimulate the production of the mucosal IgA immune response.

To this end, a series of developments for intranasal or oral administration of influenza virus vaccines has been developed. Thus, for example, the administration of an inactivated virus vaccine (Waldman et al., 1968, Nature 218:594–595), an inactivated vaccine combined with carboxyvinyl polymer (Oka et al., 1990, Vaccine 8:573–576), or with pertussis toxin B oligomer (Oka et al., 1994, Vaccine 12:1255–1258), a split virus vaccine with cholera toxin, E. coli heat-labile enterotoxin or liposomes (Tamura et al., 1992, J. Immunol. 149:981–988, Komasse et al., 1998, Vaccine 16:248–254, de Haan, 1995, Vaccine 13:155–162), an emulsion inactivated vaccine (Avtushenko et al., 1996, J. Biotechnol. 44:21–28), or a cold adapted live attenuated influenza virus vaccine (Belshe et al., 1998, N. Engl. J. Med. 338:1405–1412) produces not only the induction of HAI-IgG antibodies in the serum, but also the secretion of IgA antibodies of the mucosal membrane as well.

Inactivated viruses as orally or nasally applied vaccines must, however, be given in high concentrations in order to bring about a significant increase of antibodies. The administration of inactivated influenza virus or antigen in convenient commercial doses, free of side effects, with nasal or oral administration, does not produce a satisfactory immune response without the use of an adjuvant. (Chen et al., 1989, Current Topics in Microbiology and Immunology 146:101–106, Couch et al., 1997, J. Infect. Dis. 176:38–44). Thus, for example, for the optimum induction of the immune response with oral administration of an emulsion-inactivated vaccine, an antigen content between 66 µg antigen/dose and 384 µg antigen/dose is required (Avtushenko et al., 1996, J. Biotechnol. 44:21–28). Thus, this dose lies far above that of an inactivated vaccine for parenteral administration, which is at approximately 15 µg antigen/dose.

Although cholera toxin, E. coli heat-labile toxin and pertussis toxin have an effective adjuvant effect in oral or nasal administration of influenza antigen, they are not used for human application because of the toxic side effects. The only adjuvant approved to date for application to humans is aluminum.

A cold-adapted, live attenuated influenza virus vaccine to be found in clinical studies for nasal administration is based on virus antigens from which reassortants must be produced annually by means of genetic methods, in which the genes for the hemagglutinin and neuramidase antigens of the corresponding influenza A or B strain are transferred to an attenuated, cold-adapted master virus strain. This method is very time consuming and labor intensive. In addition, there is the danger that through reversion the attenuated virus back mutates into a virulent virus and thus can trigger viremia. When immunization is carried out with living viruses there is also a further spread in the body of the immunized individual. When cold-adapted viruses are used, there is also the constant necessity of storing the virus vaccine below the freezing point, as close to –20° C. as possible, which then requires the absolute maintenance of a chain of refrigeration to ensure sufficient storage life of the vaccine.

Eggs are used for the production of the virus reassortants and the propagation of the vaccine viruses, which entails the risk that any contaminating infectious agents that may be present may be transferred into the eggs. The purification of live viruses is also not without problems because they represent infectious material and thus a higher standard of security must be maintained.

The problem of the present invention is, therefore, to make available an influenza virus vaccine composition that does not have the disadvantages described above, and that effectively induces the IgA and IgG immune response in mammals.

BRIEF SUMMARY OF THE INVENTION

The problem is solved according to the invention by the use of a vaccine composition containing at least one inactivated influenza virus or influenza virus antigen and aluminum as an adjuvant for nasal or oral administration. The composition described is suitable in particular as a vaccine for the prophylaxis of influenza virus infections.

In the context of the present invention, it was shown that an inactivated influenza virus vaccine containing aluminum as adjuvant for nasal or oral administration triggers an effective IgG as well as IgA immune response in mammals. This was especially surprising because with the approaches to date towards the development of effective influenza virus vaccines it was found that the adjuvant effect of aluminum in elevating the immunogenicity of the antigen is very slight, even in a vaccine for parenteral administration (Davenport et al., 1968, J. Immunol. 100:1139–1140).

Furthermore, it was found that with the nasal or oral application of the vaccine composition according to the invention a considerably higher IgG and IgA titer as well as a higher HAI titer is achieved in mammals than with the vaccine formulations known to date that contain either only inactivated influenza viruses, inactivated viruses with cholera toxin, or live viruses (Table 1).

Therefore, the application according to the invention is suitable in particular for the induction of a protective mucosal IgA and a systemic IgG immune response.

Since aluminum is the only adjuvant approved for application in humans, the application, according to the invention, of the vaccine combination of inactivated influenza virus and aluminum has the great advantage that it can be administered directly to humans without any problem. The special advantage of the use according to the invention, therefore, aside from the elevated immunoreactivity of the vaccine composition for nasal or oral administration is that through use of an adjuvant that has been tested over a number of years and whose application to humans is approved, the vaccine is completely free of side effects.

DETAILED DESCRIPTION

For use according to the invention, the composition can contain aluminum preferably in the form of aluminum hydroxide $(Al(OH)_3)$ or aluminum phosphate $(AlPO_4)$. In this case, the concentration of the aluminum is preferably in a final concentration of 0.05% to 0.5%.

The influenza virus antigen quantity in the vaccine in this case is the customary antigen quantity for a vaccine dose. Preferably, the antigen quantity that is contained in a vaccine dose is between 1.5 μg antigen/dose to 50 μg antigen/dose in humans.

The influenza virus antigen can be produced from infected eggs via conventional methods, and purified.

Preferably, however, the virus antigen is obtained from an infected cell culture, such as described, for example, in WO 96/15231. Particularly preferred for the use according to the invention to produce an influenza virus vaccine is an influenza virus antigen that is obtained from a VERO cell culture infected with influenza virus that is cultured in a serum and protein-free medium. The virus antigen obtained from the infected cell culture is first inactivated with formalin and can then be obtained as a purified, concentrated virus antigen preparation by means of continuous density gradient centrifugation, DNAse treatment, diafiltration, and sterile filtration. This concentrated preparation can then be used together with aluminum as an adjuvant for the use according to the invention to produce a vaccine for nasal or oral administration.

A special advantage in the production of the vaccine is that the virus material is inactivated before purification, and so in comparison to the purification of attenuated live viruses, a considerably higher degree of purity of the antigen preparation is achieved.

A particular advantage in the use of influenza virus antigens obtained from a serum and protein-free cell culture infected with influenza virus is the absence of egg-specific proteins that could trigger an allergic reaction against these proteins. Therefore, the use according to the invention is especially suitable for the prophylaxis of influenza virus infections, particularly in populations that constitute higher-risk groups, such as asthmatics, those with allergies, and also people with suppressed immune systems and the elderly.

The vaccine can be applied in different ways.

According to one embodiment of the invention, the intranasal administration is via the mucosal route. The intranasal administration of the vaccine composition can be formulated, for example, in liquid form as nose drops, spray, or suitable for inhalation, as powder, as cream, or as emulsion.

The composition can contain a variety of additives, such as stabilizers, buffers, or preservatives.

For simple application, the vaccine composition is preferably supplied in a container appropriate for distribution of the antigen in the form of nose drops or an aerosol.

According to another embodiment of the invention, the administration is oral and the vaccine may be presented, for example, in the form of a tablet or encased in a gelatin capsule or a microcapsule, which simplifies oral application. The production of these forms of administration is within the general knowledge of a technical expert.

The invention will be explained in more detail on the basis of the following examples, whereby it is not limited to the examples.

EXAMPLES

Example 1

Production of an Influenza Virus Vaccine Preparation.

Influenza virus was obtained from a protein-free VERO cell culture infected with influenza A or B virus strain, according to WO 96/15231 or according to conventional methods from allantoic fluid from infected, incubated chicken eggs.

For the production of an inactivated influenza virus preparation from cell culture, the supernatant of an infected VERO cell culture to which formalin (final concentration 0.025%) was added, and the viruses were inactivated at 32° C. for 24 h. This material was purified by zonal centrifugation in a continuous 0–50% sucrose gradient, DNAse treatment, diafiltration, and sterile filtration. The purified material was stored at −70° C. The final product was tested for residual contamination and the following criteria were established per dose:

| | |
|---|---|
| Hemagglutinin content: | ≧15 μg HA per strain |
| Protein content: | ≦250 μg |
| Sucrose content: | ≦200 mg |
| Formalin content: | ≦5 μg |
| Benzonase content: | ≦5 ng |
| Residual DNA (VERO): | ≦100 pg |
| Endotoxin content: | ≦100 EU |
| Pyrogen: | free |

Example 2

Intranasal Immunization of Mice with Different Influenza Virus Preparations.

The antigen preparations from Example 1 were diluted in PBS to an HA antigen content of 15 μg/mL and optionally $Al(OH)_3$ added to a final concentration of 0.2%, or cholera toxin. For the production of a preparation for intranasal immunization of mice, the solution was diluted to the appropriate quantity of antigen with PBS, optionally containing $Al(OH)_3$ or cholera toxin.

Four Balb/c mice each received intranasal immunization with different influenza virus preparations, and in each case, 50 μL of a solution containing influenza virus antigen and optionally an adjuvant were administered drop-wise into the nostrils of the mice. The first immunization was given on Day 0, the second on Day 7, and the third on Day 14. On the 28th day the IgG, IgA, and HAI titers in serum, saliva, and pulmonary lavage were determined.

Table 1 shows the plan of the intranasal immunization of the individual mice groups with different influenza virus preparations.

TABLE 1

Vaccination plan for the intranasal immunization of mice

| Group Balb/c mice | Antigen | Dose | Route |
|---|---|---|---|
| 1. Group | Inactivated whole viruses from VERO cells | 1 $\mu$g HA | 50 $\mu$ l/i.n. |
| 2. Group | Inactivated whole viruses from infected eggs | 1 $\mu$g HA | 50 $\mu$ l/i.n. |
| 3. Group | Live viruses from VERO cells | $5 \times 10^6$ $EID_{50}$ | 50 $\mu$ l/i.n. |
| 4. Group | Live viruses from infected eggs | $5 \times 10^6$ $EID_{50}$ | 50 $\mu$ l/i.n. |
| 5. Group | VERO mock preparation | 5% of 1 $\mu$g | 50 $\mu$ l/i.n. |
| 6. Group | Egg mock preparation | 5% of 1 $\mu$g | 50 $\mu$ l/i.n. |

Example 3

Determination of the IgA Titer in the Saliva, Pulmonary Lysate, and Serum, as well as of the IgG Titer and HAI Titer in the Serum.

On Day 28 after immunization, saliva, pulmonary, and serum specimens were taken from the animals, and the antibody titer in the individual specimens was determined.

Saliva specimens were collected by injection of 0.5 mL PBS into the oral cavity of the mouse, and the presence of IgA antibodies was tested.

To produce pulmonary lysate specimens, the mice were killed, the thorax opened, and the lungs removed and washed with PBS. Subsequently, the lungs were ground and the homogenate centrifuged in order to remove cell tissue. The supernatant was collected and stored at −20° C. until testing for IgA antibodies.

The IgG and IgA antibody titer was determined with a commercial influenza virus Type A and B ELISA test (Genzyme Virotech). After a 2 h incubation at 37° C., the specific IgG and IgA antibodies were detected with conjugated goat anti-mouse IgG or IgA (Pharmigen) and chromogenic substrate containing $H_2O_2$ and o-phenyldiamine.

To determine the HAI titer, blood was taken from the mice, and the serum obtained was tested in the influenza A or B hemagglutination test (HAI titer) according to the method of Palmer et al. (1975, Advanced laboratory technicals [sic; techniques] for immunological diagnostic, U.S. Dept. Health. Ed. Welfare. P.H.S. Atlanta, Immunology Ser. No. 6, Procedural guide, part 2, hemagglutination inhibition test, pp. 25–62).

Table 2 shows a summary of the determination of the IgA antibody titer in the saliva, pulmonary lysate, and serum, and the IgG antibody titer as well as HAI titer in the serum. The data clearly indicate that neither the IgA nor the IgG immune response is stimulated by an inactivated whole virus vaccine without adjuvant. On the other hand, if the immunization is done with live virus or inactivated whole virus to which cholera toxin has been added, an increase of the IgA, IgG, and HAI titers takes place in the mice, just as after immunization with inactivated whole virus to which aluminum has been added, whereby with the latter vaccine, the IgG immune response in the serum was actually the highest of all preparations tested. Likewise, the highest HAI titer was measured for the inactivated vaccine with aluminum.

The results show that the intranasal immunization with inactivated influenza virus vaccine to which aluminum has been added induces a slightly increased IgA immune reaction in comparison to the known influenza virus vaccine preparations, and a considerably higher IgG immune response in mammals, without having the disadvantages of a live virus vaccine or a vaccine to which an adjuvant has been added that has not been approved for application to humans, such as cholera toxin.

Example 4

Storage Stability of the Vaccine Composition at Different Temperatures

For stability investigations, the monovalent bulks (MB) of the influenza virus vaccination strains Johannesburg 82, Nanchang and B/Harbin were stored for 12 months at +4° C., −20C., and −80° C. After 6 and 12 months, the specific hemagglutination test (HA) content of the MBs Johannesburg 82 (MB/J/0197), Nanchang (MB/N/0197), and B/Harbin (MB/H/0397) without Pluronic, as well as Johannesburg 82 (MB/J/0297P), Nanchang (MB/N/0297P), and B/Harbin (MB/H/0497P) with Pluronic was determined by means of a SRD (single radial immunodiffusion) assay according to Wood et al., 1977, J. Biol. Standard 5:237–247, and the deviation from the initial value was calculated in percent.

The trivalent bulks (TVB) 410197 (without Pluronic) and 4102997P (with Pluronic) were also stored for 12 months at +4° C., and then tested in the SRD assay. Furthermore, the reserve samples of these MBs and TVBs that had been stored at room temperature for sterility testing were analyzed in the SRD assay after 12 months.

The Results of the MBs are Given in Table 3, and the Results of the TVBs in Table 4:

The storage of the MBs at +4° C. and −80° C. for 1 year show practically no reduction of the specific HA content compared with the initial value in the case of Johannesburg, 82 and Nanchang. The B/Harbin preparations appear to be less stable; they drop by about 25% (without Pluronic) and about 40% (with Pluronic). Storage at −20° C. appears to have a significant influence on the stability; for Johannesburg 82, the values drop by 27% (without Pluronic) or 11% (with Pluronic), for Nanchang by 9% (without Pluronic) or 19% (with Pluronic), and for B/Harbin by 34% (without Pluronic) or 47% (with Pluronic). The results of storage at room temperature indicate an astounding stability of the preparation. For Johannesburg 82, approximately 80% of the original HA content can still be detected, for Nanchang ca. 65%, and for B/Harbin about 45%. Storage of the TVBs at +4° C. for 1 year again shows no significant difference in the HA content. The stability of the TVBs at room temperature for 1 year differs in the 3 strains: for Johannesburg 82 there is no significant difference in the HA content, for Nanchang a slight reduction (about 10%), and for B/Harbin a drop of approximately one third.

Overall, the preparations are very stable, even with storage at room temperature, and there is no significant difference between the preparations with and without Pluronic.

This application claims priority to A194/99 filed Feb. 11, 1999, the entirety of which is hereby incorporated by reference.

TABLE 2

Intranasal immunization of mice with different influenza preparations,
and determination of the IgA titer in the saliva, pulmonary
lysate, and serum and the IgG titer as well as HAI titer in the serum

| | | | Titer | | | | | | | | | | |
|---|---|---|---|---|---|---|---|---|---|---|---|---|---|
| | | | IgA | | | | | | IgG | | HAI | | |
| | | | Saliva | | Pulmonary lysate | | Serum | | Serum | | Johann 82 | Nanchang | B/Harbin |
| Immunogen | Strain | Adjuvant | Flu A | Flu B | Flu A | Flu B | Flu A | Flu B | Flu A | Flu B | A/H1N1 | A/H3N2 | B |
| Vero Vaccine | J, N, H | — | <10 | <10 | <10 | <10 | <10 | <10 | 800 | 100 | 80 | 80 | 20 |
| (inactivated) | | Al(OH)$_3$ | 40 | 10 | 320 | 40 | 160 | <10 | 102.400 | 3.200 | 1.280 | 640 | 160 |
| | | CTB | 20 | 10 | n.b. | n.b. | 80 | <10 | 51.200 | 12.800 | 640 | 640 | 160 |
| Egg vaccine | J, N, H | — | 10 | 10 | 10 | <10 | <10 | <10 | 1,600 | 100 | 160 | 160 | 40 |
| (inactivated | | Al(OH)$_3$ | 40 | 20 | 320 | 40 | 160 | 10 | 51.200 | 6.400 | 640 | 320 | 160 |
| Live virus, Vero | N | — | 20 | <10 | n.b. | n.b. | 160 | <10 | 51.200 | <10 | 80 | 640 | <10 |
| Live virus, egg | N | — | 40 | <10 | n.b. | n.b. | 160 | <10 | 51.200 | <10 | 80 | 320 | 20 |
| Vero Mock | | — | <10 | <10 | <10 | <10 | <10 | <10 | <10 | <10 | 80 | 160 | 20 |
| | — | Al(OH)$_3$ | <10 | <10 | n.b. | n.b. | <10 | <10 | <10 | <10 | 80 | 160 | <10 |
| | | CTB | <10 | <10 | n.b. | n.b. | <10 | <10 | <10 | <10 | 80 | 160 | <10 |
| Egg Mock | — | — | <10 | <10 | <10 | <10 | <10 | <10 | <10 | <10 | 80 | 160 | 20 |
| | — | Al(OH)$_3$ | <10 | <10 | <10 | <10 | <10 | <10 | <10 | <10 | 80 | 160 | 20 |

J: Johannesburg 82 (A/H1N1),
N: Nanchang (A/H3N2),
H: B/Harbin, n.b. = not determined

TABLE 3

Storage stability of the MBs of influenza vaccine for the season 1997/98 !

| | Lot | Storage | 0 Months | 6 Months | 12 Months |
|---|---|---|---|---|---|
| Johannesburg 82 | MB/J0197 | +4° C. | 184 μg | 204 μg [111%] | 189 μg [103%] |
| | | −20° C. | | 182 μg [99%] | 134 μg [73%] |
| | | −80° C. | | 210 μg [114%] | 187 μg [102%] |
| | | RT | | — | 152 μg [83%] |
| | MB/J/0297P | +4° C. | 198 μg | 230 μg [116%] | 207 μg [105%] |
| | | −20° C. | | 202 μg [102%] | 177 μg [89%] |
| | | −80° C. | | 226 μg [114%] | 212 μg [107%] |
| | | RT | | — | 161 μg [81%] |
| Nanchang | MB/N0197 | +4° C. | 126 μg | 130 μg [103%] | 131 μg [104%] |
| | | −20° C. | | 124 μg [98%] | 115 μg [91%] |
| | | −80° C. | | 143 μg [114%] | 132 μg [105%] |
| | | RT | | — | 83 μg [66%] |
| | MB/N/0297P | +4° C. | 140 μg | 128 μg [91%] | 134 μg [96%] |
| | | −20° C. | | 139 μg [99%] | 113 μg [81%] |
| | | −80° C. | | 143 μg [102%] | 150 μg [107%] |
| | | RT | | — | 90 μg [64%] |
| B/Hardin | MB/H/0397 | +4° C. | 116 μg | 89 μg [77%] | 83 μg [72%] |
| | | −20° C. | 324 μg | 101 μg [87%] | 76 μg [66%] |
| | | −80° C. | | 97 μg [84%] | 88 μg [76%] |
| | | RT | | — | 148 μg [46%] |
| | MB/H/04/97P | +4° C. | 146 μg | 95 μg [65%] | 87 μg [60%] |
| | | −20° C. | 374 μg | 108 μg [74%] | 77 μg [53%] |
| | | −80° C. | | 105 μg [72%] | 89 μg [61%] |
| | | RT | | — | 159 μg [43%] |

RT: Room temperature
P: with Pluronic
Data on the specific hemagglutination (HA) content given per mL and in brackets, data on
the HA content compared to the initial value given in percent

TABLE 4

Storage stability of the influenza vaccine for the season 1997/98 II
Storage of the TVBs (trivalent bulk) at +4° C. and at room temperature

| | | | | Storage | |
| --- | --- | --- | --- | --- | --- |
| | | | | 12 months | |
| Strain | Lot | Pluronic | 0 Months | +4° C. | Room temperature |
| Johannesburg 82 | 410198 | − | 16.8 μg | 17.5 μg [104%] | 15.8 μg [94%] |
| Nanchang | 410198 | − | 15.9 μg | 16.3 μg [103%] | 14.1 μg [89%] |
| B/Harbin | 410198 | − | 16.3 μg | 14.1 μg [87%] | 10.6 μg [65%] |
| Johannesburg 82 | 410298P | + | 16.9 μg | 17.4 μg [103%] | 17.3 μg [102%] |
| Nanchang | 410298P | + | 15.4 μg | 13.9 μg [90%] | 13.9 μg [90%] |
| B/Harbin | 410298P | + | 14.5 μg | 14.1 μg [97%] | 9.7 μg [67%] |

Data on the specific hemagglutination (HA) content per dose (=0.5 mL), and in brackets data on the change of the HA content compared to the initial value given in percent

What is claimed is:

1. A method for the production of an influenza virus vaccine for nasal or oral administration comprising combining an inactivated influenza virus with aluminum in a composition suitable for nasal or oral administration, wherein the composition is free of media and egg proteins.

2. The method of claim 1, wherein the inactivated influenza virus is obtained from an infected cell culture.

3. The method of claim 2, wherein the infected cell culture is incubated in a serum- and protein-free medium.

4. The method of claim 1, wherein the inactivated influenza virus is subjected to purification after its inactivation.

5. A method for the production of an influenza virus vaccine that is formulated for nasal or oral administration, wherein the method comprises combining influenza virus antigen obtained from a mammalian cell culture comprising protein-free media with an aluminum salt in a composition suitable for nasal or oral administration, wherein the composition is free of media and egg proteins.

6. The method according to claim 5, wherein aluminum salt is aluminum hydroxide or aluminum phosphate.

* * * * *